United States Patent [19]

Hay

[11] Patent Number: 5,237,062
[45] Date of Patent: Aug. 17, 1993

[54] POLYMERS DERIVED FROM PHENOLPHTHALEINS

[76] Inventor: Allan S. Hay, 5015 Glencairn Avenue, Montreal, Quebec, Canada, H3W 2B3

[21] Appl. No.: 931,310

[22] Filed: Aug. 18, 1992

Related U.S. Application Data

[63] Continuation-in-part of Ser. No. 874,683, Apr. 28, 1992, abandoned.

[51] Int. Cl.$^5$ .................................. C07D 237/32
[52] U.S. Cl. ........................................ 544/237
[58] Field of Search ............................ 544/237

[56] References Cited

U.S. PATENT DOCUMENTS 3,813,384  5/1974  Vogelsang .
4,350,813  9/1982  Takei et al. ............. 544/237
4,464,532  8/1984  Takei et al. ............. 544/237

OTHER PUBLICATIONS

J. Am. Chem. Soc. 39, 679 (1917), W. R. Orndorff et al.
Vol. 68, p. 718 (Apr. 1946)-Hubacher-J. Am. Chem. Soc.
Acta. Chem. Scand. 14, 359 (1960), Lund.
Pages 1506-1514, N. Dennis et al, J. Chem. Soc. Perkin.
Chem. Ab. vol. 91, 1979, 107991e, N. Kitagawa et al.
Polish Journal of Chemistry 55, pp. 995-1005 (1981).

*Primary Examiner*—John Kight, III
*Assistant Examiner*—Shelley A. Dodson
*Attorney, Agent, or Firm*—Swabey Ogilvy Renault

[57] ABSTRACT

Homopolymers and copolymers with high Tg's are produced from phthalazones which in turn are produced from phenolphthalein as a readily available starting material; the homopolymers may be represented by formula (IX):

Homopolymer (IX):

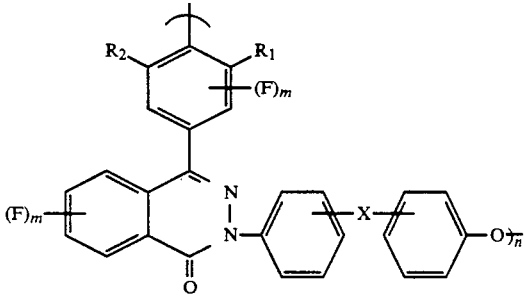

wherein $R_1$ and $R_2$, which may be the same or different, are selected from hydrogen, fluorine, phenyl and fluorophenyl, each m, which may be the same or different, is an integer of 0, 1, 2, 3 or 4, and n is an integer of 2 to 200. Novel phenyl substituted phenolphthaleins and novel hydroxybenzoylbenzoic acids, as well as novel phthalazones, all of which may be employed in the preparation of homopolymers and copolymers of the invention, are also provided.

2 Claims, 1 Drawing Sheet

POLYMERS DERIVED FROM PHENOLPHTHALEINS

CROSS-REFERENCE TO RELATED APPLICATIONS

This application is a continuation-in-part of U.S. application Ser. No. 07/874,683, now abandoned, filed Apr. 28, 1992.

BACKGROUND OF THE INVENTION

1. Field of the Invention

This invention relates to novel polymers having N-phthalazone and ether linkages and their preparation; the invention also relates to certain novel phthalazones useful in the manufacture of the polymers, and their preparation; the invention also relates to certain novel substituted phenolphthaleins and hydroxybenzoylbenzoic acids, and processes for producing them, which are useful in an economic route for the manufacture of the polymers; the invention also relates to a process for producing valuable substituted 4-aminophenols, and to novel substituted 4-aminophenols.

2. Brief Description of Prior Art phenolphthalein is readily synthesized from phthalic anhydride and phenol in the presence of a strong acid catalyst. It has been used principally as a laxative and as a chemical indicator since in the presence of base it turns deep red.

The reaction is illustrated by the following scheme:

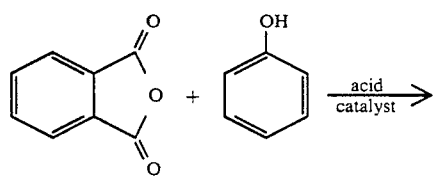

Polymers have been synthesized from phenolphthalein including polyesters, polycarbonates and poly(ether ketone)s, and they generally have high glass transition temperatures. For example, Morgan (P. Morgan, J. Pol. Sci. A2, 437 (1964)) synthesized polyesters and polycarbonates from phenolphthalein. However, because the molecule is not symmetrical the polymers are amorphous, and problems often arise in the synthesis Of these polymers as well as in the processing of the materials because of reactions involving the lactone ring. A poly(ether ketone) has been synthesized from phenolphthalein (G. Qipeng, H. Jinyu & C. Tianlu, J. Appl. Pol. Sci. 42, 2851 (1991)), in accordance with the following reaction scheme:

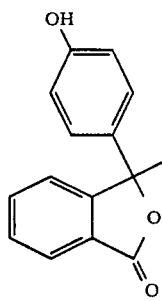

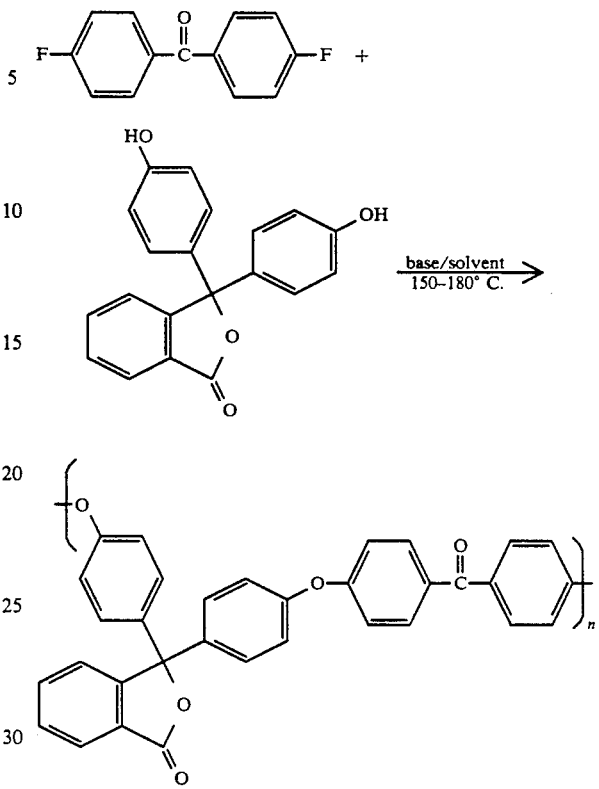

This polymer is amorphous and is produced under relatively moderate conditions.

In contrast the commercially available PEEK is produced only at relatively high temperatures and is a highly crystalline, very insoluble material. The production of PEEK is described in U.S. Pat. No. 4,320,224 and is illustrated in the following reaction scheme:

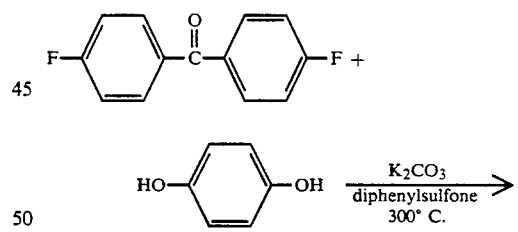

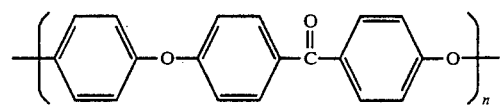

PEEK

As a result of the aforementioned problems with the polymers synthesized from phenolphthalein by Morgan, such polymers have not been developed commercially.

It has been known for many years that when phenolphthalein reacts with hydroxylamine an intermediate which was thought to be an oxime, forms which on treatment with acid yields 4-aminophenol and 2(4-hydroxybenzoyl)benzoic acid as products (P. Friedlander, Chem. Ber. 26, 172 (1893)). On further treatment of this intermediate with hydroxylamine hydrochloride 4-aminophenol and 4-hydroxyphenyl N-phthalimide are formed. The mechanism of this reaction and the structure of this intermediate was obscure until the work of Lund (H. Lund, Acta Chem. Scand. 14, 359 (1960)) who determined that the intermediate "oxime" was instead the anil of 4-aminophenol with 2-(4-hydroxybenzoyl)-benzoic acid.

The reactions described above involving the anil are illustrated in the following reaction scheme:

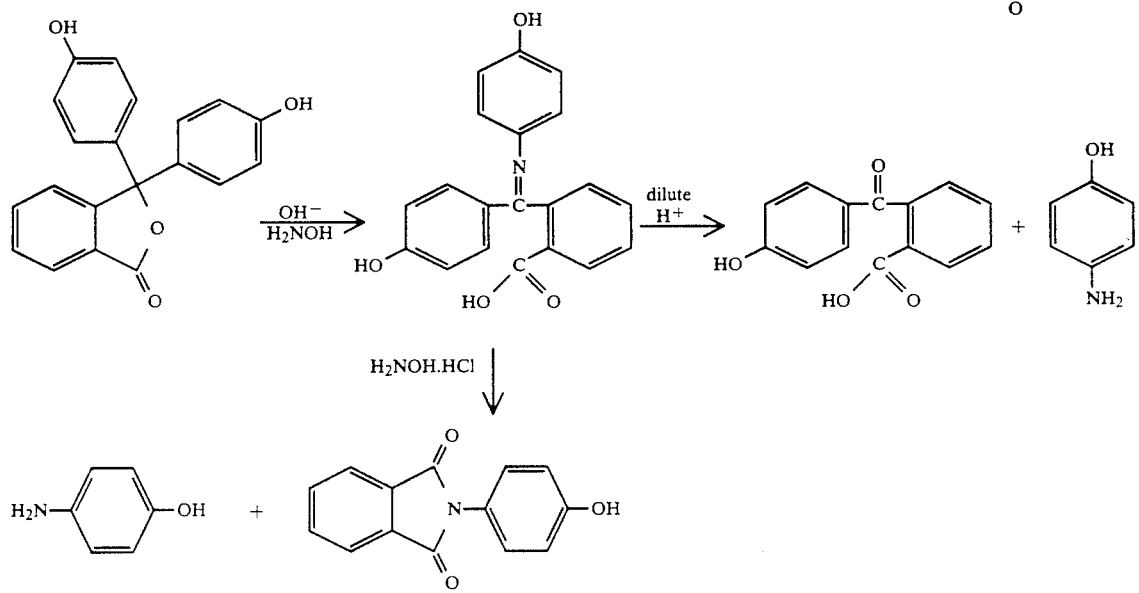

It has been demonstrated that reaction of 2-(4-hydroxybenzoyl)benzoic acid with phenol produces phenolphthalein and that reaction with substituted phenols gives unsymmetrically substituted phenolphthaleins as products (W. R. Orndorff and R. R. Murray, J. Am. Chem. Soc. 39, 679 (1917)) which would be difficult to prepare by the direct reaction of a phenol with phthalic anhydride. Since it would require separation of unsubstituted, monosubstituted and disubstituted phenolphthaleins.

This reaction is illustrated by the following reaction scheme:

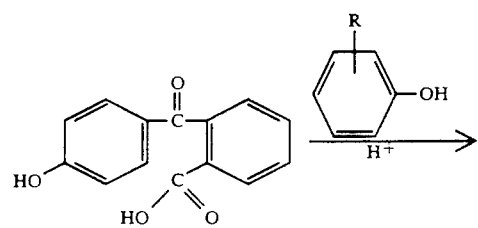

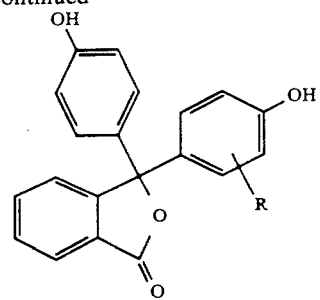

SUMMARY OF THE INVENTION

It is an object of this invention to provide polymers of high glass transition temperature having N-phthalazone and ether linkages.

It is a further object of this invention to provide an economic process for producing the polymers from readily available starting materials.

It is still another object of this invention to provide novel phthalazones useful in the manufacture of the polymers.

It is yet another object of this invention to provide a process for producing the novel phthalazones.

Still further it is an object of this invention to provide certain novel hydroxybenzoic Still further it is an object of this invention to provide certain novel hydroxybenzoic acids, and processes for their preparation, useful in the manufacture of phthalazones and thus of the polymers.

It is a still further object of this invention to provide novel substituted phenolphthaleins, and processes for their preparation, which are useful in the manufacture of hydroxybenzoylbenzoic acids, and thus of the polymers.

Still further it is an object of this invention to provide a process for producing substituted 4-aminophenols, and processes for their preparation.

In accordance with one aspect of the invention there is provided novel polymers of formula (X), as described hereinafter, and in particular novel homopolymers of formula (IX), as described hereinafter.

In accordance with another aspect of the invention there is provided processes for producing the novel polymers of formula (X) and the novel homopolymers of formula (IX).

In accordance with still another aspect of the invention there is provided novel phthalazones of formulae (VII), as described hereinafter.

In accordance with a related aspect of the invention there is provided processes for producing the phthalazones (VII).

In accordance with yet another aspect of the invention there is provided novel hydroxybenzoic acids of formula (IV), as described hereinafter.

In accordance with another aspect of the invention there is provided a process for producing hydroxybenzoic acids (V) which produces 4-aminophenols (XV) as a valuable by-product.

In accordance with still another aspect of the invention there is provided novel phenyl substituted phenolphthaleins of formula (I), as described hereinafter.

In accordance with a related aspect of the invention there is provided a transalkylation process for producing the phthaleins (I).

The process of producing the polymers (X) is illustrated in Scheme A hereinafter.

The process of producing the phthalazones (VII) is illustrated in Scheme B hereinafter.

The transalkylation process for producing the phthaleins (I) is illustrated in Scheme C hereinafter.

The process of producing hydroxybenzoylbenzoic acids (V) including the novel acids (IV), and by-product substituted 4-aminophenols is illustrated in Scheme D hereinafter.

Scheme E hereinafter shows a particular process for producing phthalazones of the invention from phenolphthaleins.

Scheme F hereinafter shows a particular process for producing poly(ether ketone)s and poly(ether sulfone)s from the phthalazones of Scheme E.

Polymer (X):

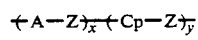

Homopolymer (IX):

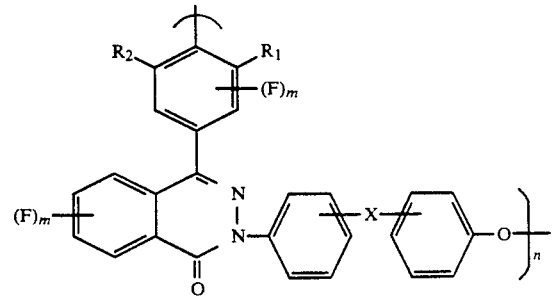

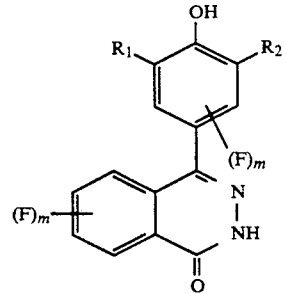

Hydroxybenzoylbenzoic acid (IV):

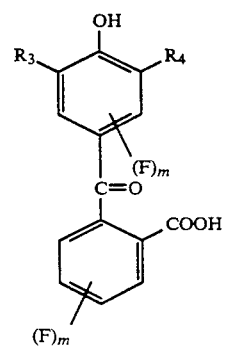

Phenyl Substituted Phenolphthaleins (I):

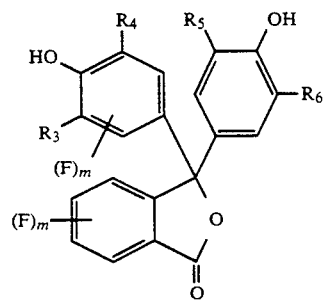

Polymer XXI

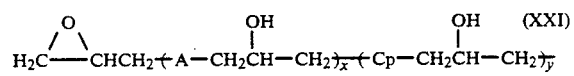

Reaction Scheme A

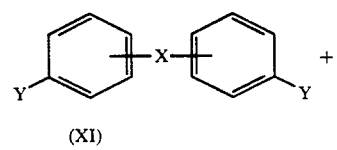

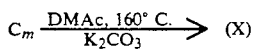

Phthalazone (VII):

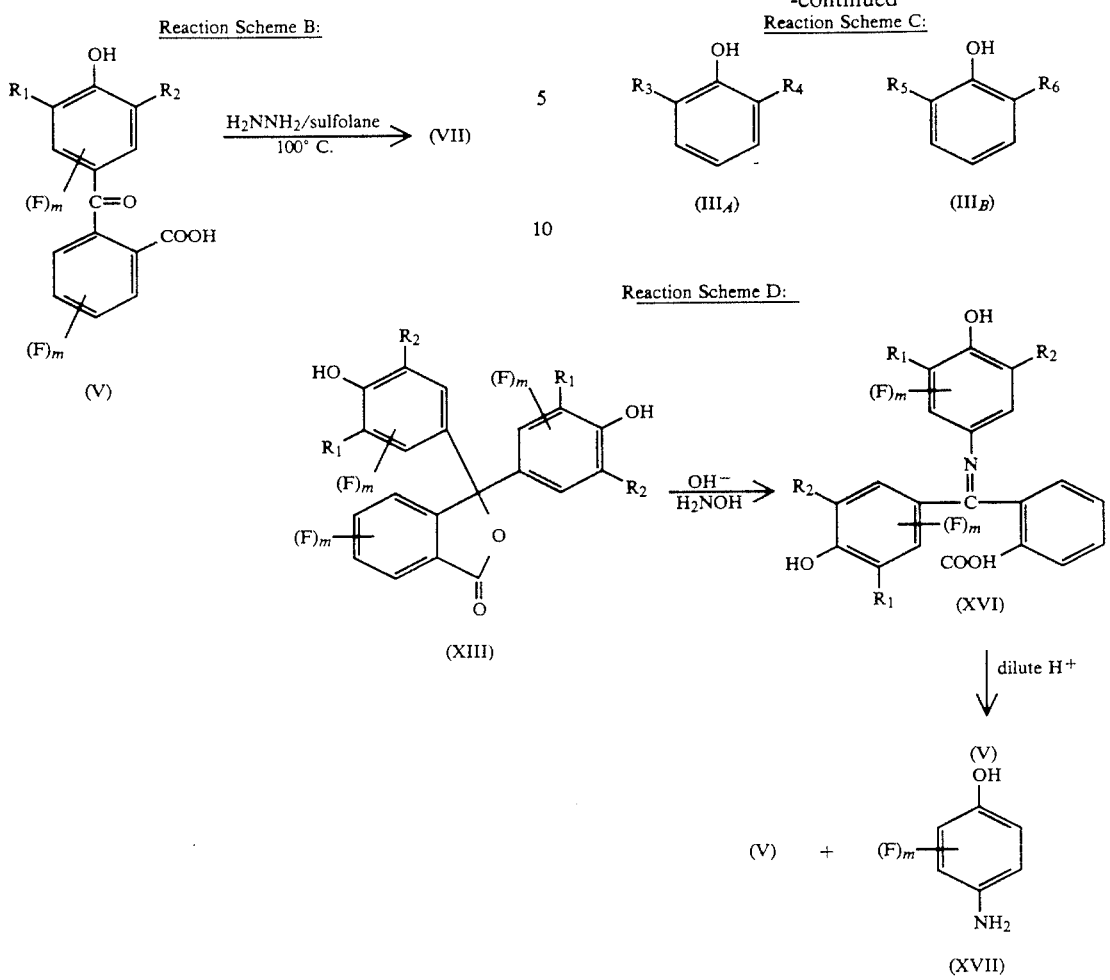
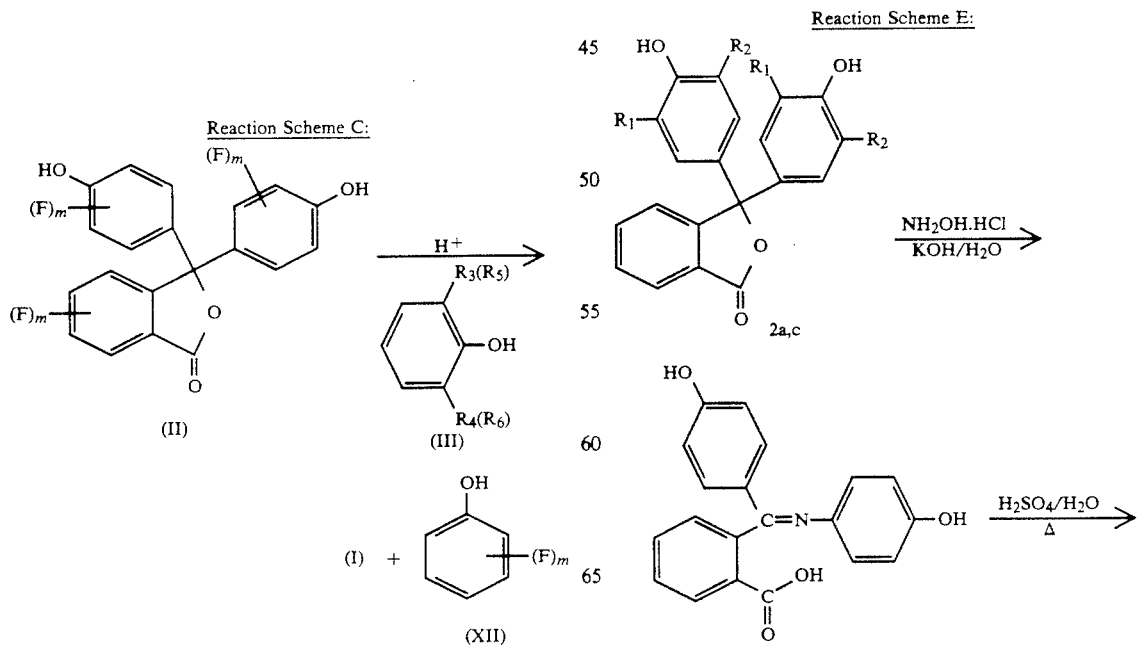

9
-continued
Reaction Scheme E:
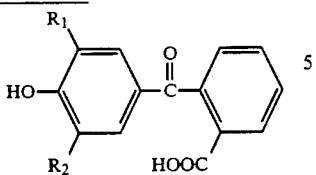
3a; R1 = H
　　R2 = Ph
3b; R1 = R2 = Ph
3c; R1 = R2 = H
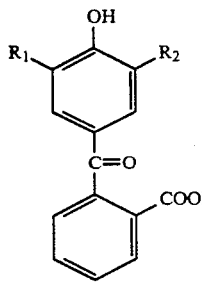
3a-c
10
-continued
Reaction Scheme E:
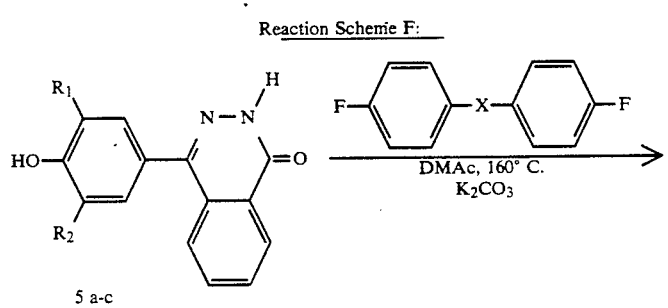
4a; R1 = H
　　R2 = Ph
4b; R1 = R2 = Ph
4c; R1 = R2 = H
Reaction Scheme F:
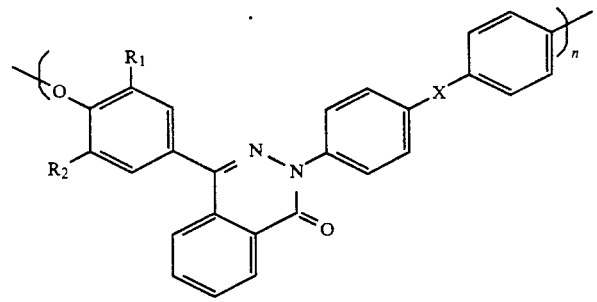
5 a-c
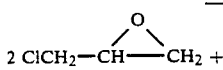
6a; X = O=S=O
6b; X = C=O
　　R1 = R2 = H
7a; X = O=S=O
7b; X = C=O
　　R1 = H, R2 = Ph
8a; X = O=S=O
8b; X = C=O
　　R1 = R2 = Ph
Reaction Scheme G:
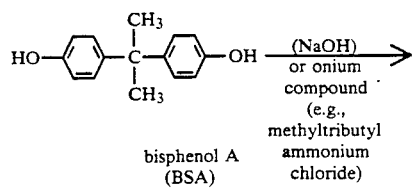
epichlorohydrin
bisphenol A (BSA)   (NaOH) or onium compound (e.g., methyltributyl ammonium chloride)

-continued
Reaction Scheme G:

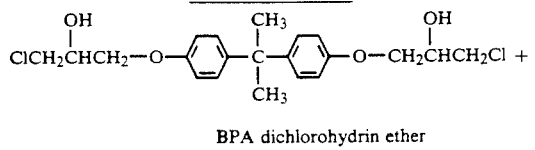

BPA dichlorohydrin ether

2 NaOH ⟶

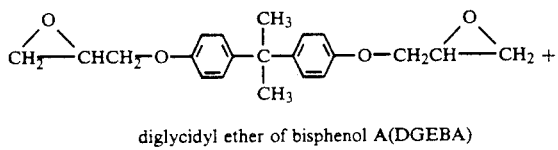

diglycidyl ether of bisphenol A(DGEBA)

2NaCl + 2H₂O

In the above formulae and reaction schemes A, B, C and D:

—A— is a radical of formula (XIV):

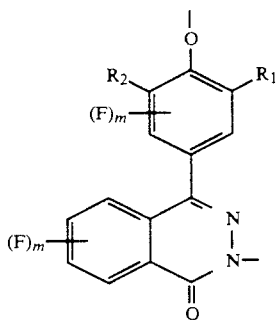

Z is a radical

a phthaloyl radical of the formula:

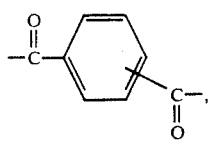

an imide radical of formula:

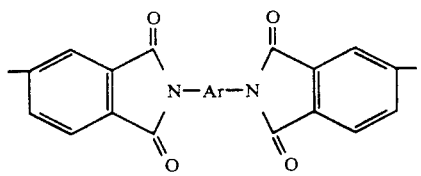

wherein Ar is arylene, especially phenylene or biphenylene, a urethane radical of formula:

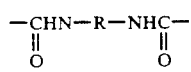

in which R is an aliphatic or aromatic radical, or a radical of formula (XV):

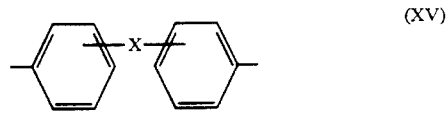

Cp is the radical —A— of formula (XIV) or is derived from a comonomer $C_m$;

R₁ and R₂ are the same or different and are each selected from hydrogen, phenyl and fluorophenyl;

R₃, R₄, R₅ and R₆ are the same or different and are each selected from hydrogen and fluorophenyl provided that in formula (I) at least one of R₃, R₄, R₅ and R₆ is phenyl or fluorophenyl, and in formula (IV) at least one of R₃ and R₄ is phenyl or fluorophenyl; each m, which may be the same or different, is an integer of 0, 1, 2, 3 or 4.

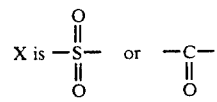

and may be meta or para, but is preferably para to the substituents of the phenyl rings which it bridges;

n is an integer of 2 to 200;

x is an integer of at least 1;

y is an integer of 1 or more;

x+y=n, and

Y is a fluorine or chlorine atom.

When R₁, R₂, R₃, R₄, R₅ and R₆ are selected from fluorophenyl, such fluorophenyl may contain 1 to 5 fluoro substituents.

The inclusion of fluorine as a substituent on one or more of the phenyl rings in the polymers increases the stability, and, in particular, increases the thermo-oxidative stability.

i) Phenolphthaleins

The novel phenyl substituted phenolphthaleins within the class (I) are compounds in which R₃, R₄, R₅ and R₆ are phenyl; preferably m is O.

The phenolphthaleins (I) are indicator dyes and the colours in basic solution go from the deep red of phenolphthalein to deeper shades of blue as the number of phenyl substituents increases.

Particularly preferred compounds (I) are those in which m is O, and:

R₃ and R₄ are both hydrogen, and R₅ and R₆ are both phenyl;

R₃, R₄, R₅ and R₆ are all phenyl;

R₄ is phenyl and R₃, R₅ and R₆ are all hydrogen;

R₃ and R₄ are both phenyl and R₅ and R₆ are both hydrogen; and

R₅ is phenyl and R₃, R₄ and R₆ are all hydrogen.

The phenyl substituted phenolphthaleins (I) are produced by the transalkylation reaction of Scheme C, which is suitably carried out by heating the reactants (II) and (III) in the presence of a strong acid, for example, methanesulfonic acid.

The transalkylation is an equilibrium reaction and therefore the by-product phenol (XI) should be removed during the course of the reaction or a large excess of the reactant (III) can be employed.

The phenol (III) may be a single phenol of formula (III$_A$) or (III$_B$) or different phenols (III$_A$) and (III$_B$) may be employed in successive steps.

In the case in which m is 0 and the by-product (XI) is phenol, the phenol is suitably removed from the reaction mixture by distillation under reduced pressure.

ii) Hydroxybenzoylbenzoic acids

The acids (V) include novel acids (IV). The acids (V) are produced from the phenolphthleins (XIII) in reaction scheme D by reaction with hydroxylamine under basic conditions followed by treatment with acid following the procedure of Friedlander described hereinbefore. The by-product 4-aminophenols (XV) represent valuable by-products.

Many polymers have been synthesized in the past from 4-aminophenol, however, it is a relatively expensive material and therefore the polymers have not been extensively exploited. The present synthesis represents a more economical approach to the material and furthermore substituted aminophenols can be readily prepared. This permits one to tailor the properties of the resulting polymers since the glass transition temperatures and the solubility can be modified by varying the substituents $R_1$ and $R_2$ and varying m.

iii) Phthalazones

Reaction of the acids (V) with hydrazine in accordance with scheme B above produces the colourless crystalline phthalazones (VII). When reacted with a base the phthalazones (VII) are converted to salts which can be used in the same way as salts of other biphenols to produce polymers, such as polyethers, polyesters, polycarbonates and polyformals.

The process of scheme B is suitably carried out at a temperature of 100° C. in sulfolane as solvent.

Particularly preferred phthalazones (VII) are those in which m is 0 and:

$R_1$ and $R_2$ are both hydrogen;
$R_1$ and $R_2$ are both phenyl; or
$R_1$ is hydrogen, and
$R_2$ is phenyl.

iv) Polymers

A variety of new polymers (X) including homopolymers (IX) can be prepared from the phthalazones (VII).

Thus referring to scheme F hereinbefore the polysulfone can be readily prepared by reaction of 4c with 4,4′-difluorodiphenylsulfone in N,N′-dimethylacetamide (DMAC) at 160° C. in the presence of potassium carbonate. The poly(ether sulfone) 6a is a highly thermo-oxidatively stable polymer with a surprisingly high glass transition temperature of 294.5° C. The poly(ether ketone) 6b from 4c can be prepared with a high molecular weight when sulfolane is used as solvent at a higher temperature and it has a Tg of 253° C. From the phenyl substituted phthalazones 4a and 4b high molecular weight poly(ether sulfone)s and poly(ether ketone)s have been synthesized. The polymers can be cast into tough flexible films and by thermogravimetric analysis it has been determined that they are highly thermoxidatively stable with 5% weight losses at around 500° C. The poly(ether sulfone)s all have higher Tg's than the corresponding poly(ether ketone)s. The poly(ether sulfone) 6a from the unsubstituted phthalazonebiphenol 4c has the highest Tg in the series whereas the monosubstituted compound 4a gives polymers with the lowest Tg's.

Polyesters, especially phthalates, polycarbonates, polyformals, polyetherimides, polyethers and polyurethanes can also be synthesized from the phthalazones (VII).

These polymers can be prepared by polymerization techniques which are well understood by persons in the art.

Thus, for example, the polymerization of the phthalazones (VII) with methylene dichloride, provides the polyformals and with an appropriate diisocyanate provides the polyurethanes; dicarboxylic acid halides are employed to produce the phthalates. The polycarbonates are produced using phosgene as the reactant with the phthalazone (VII).

The polymers of the invention have high glass transition temperatures and are thus useful in high temperature applications, as coatings, films or molded parts and components.

Many of the commercially available high performance plastics are synthesized from bisphenols. These include epoxy resins, which are made principally from bisphenol A(BPA), and engineering plastics which are materials that perform for long periods of time and meet engineering requirements for a combination of properties such as heat, chemical and fire resistance, mechanical strength, and color stability. The major applications for engineering plastics such as the polymers of the invention are as replacements for metals, ceramics and glass.

In the present invention the bisphenols or biphenols of the conventional polymers can be fully or partially replaced by the phthalazones (VII).

The ready availability of the reactants required to produce polymers (X), for example, employing schemes E and F means that the polymers can be economically produced.

Copolymers of formula (X) are, in particular, polymers in which Cp is derived from a bisphenol or biphenol, especially bisphenol A, p,p′-biphenol or hydroquinone.

The phthalazones (VII) of the invention are useful in the synthesis of the various classes of polymers described above, and produce new polymers with unique properties. These classes of polymers are conventionally prepared using bisphenol A, which is readily available. Replacing a portion of the bisphenol A with the phthalazones (VII) of the invention produces new copolymers. Thus, for example, poly(ethersulfone)s prepared from the phthalazones (VII) of the invention have much increased glass transition temperatures and improved solvent resistance. Copolymers in which a proportion of the conventionally employed bisphenol A is replaced by a phthalazone (VII) can be expected to have progressively increasing glass transition temperatures and improved solvent resistance as the proportion of bisphenol A which is replaced, is increased.

Of course, the bisphenol A can be wholly replaced by the phthalazones (VII) to produce novel homopolymers (IX).

The bisphenols and biphenols such as bisphenol A are also widely used in the manufacture of epoxy resins or diglycidyl ethers. These expoxy resins are, for example, produced by reaction of epichlorohydrin and bisphenol A. The general structure of epichlorohydrin-bisphenol A expoxy resins is shown in formula (XX):

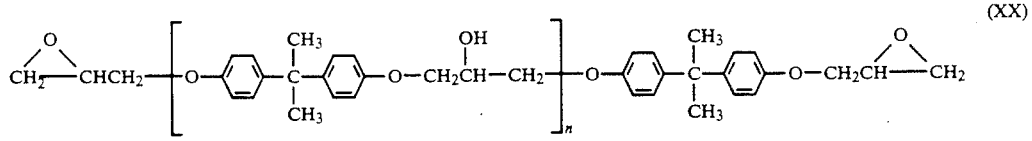

wherein each molecule consists of n+1 repeating units, n being an integer indicative of the extent of polymerization.

The reaction is illustrated in Scheme G above; as the reaction proceeds, terminal epoxide rings are opened and hydroxyl groups are formed.

In accordance with the invention the bisphenol A can be fully or partly replaced by a phthalazone (VII) of the invention to produce novel polymers (XXI) including homopolymers and copolymers. It will be understood that in the case of copolymers other biphenols can be employed in place of bisphenol A, for example, p,p'-biphenol or hydroquinone.

BRIEF DESCRIPTION OF DRAWING

The invention is further illustrated by reference to the accompanying drawing in which.

DESCRIPTION OF PREFERRED EMBODIMENTS WITH REFERENCE TO THE DRAWINGS

Figure 1:
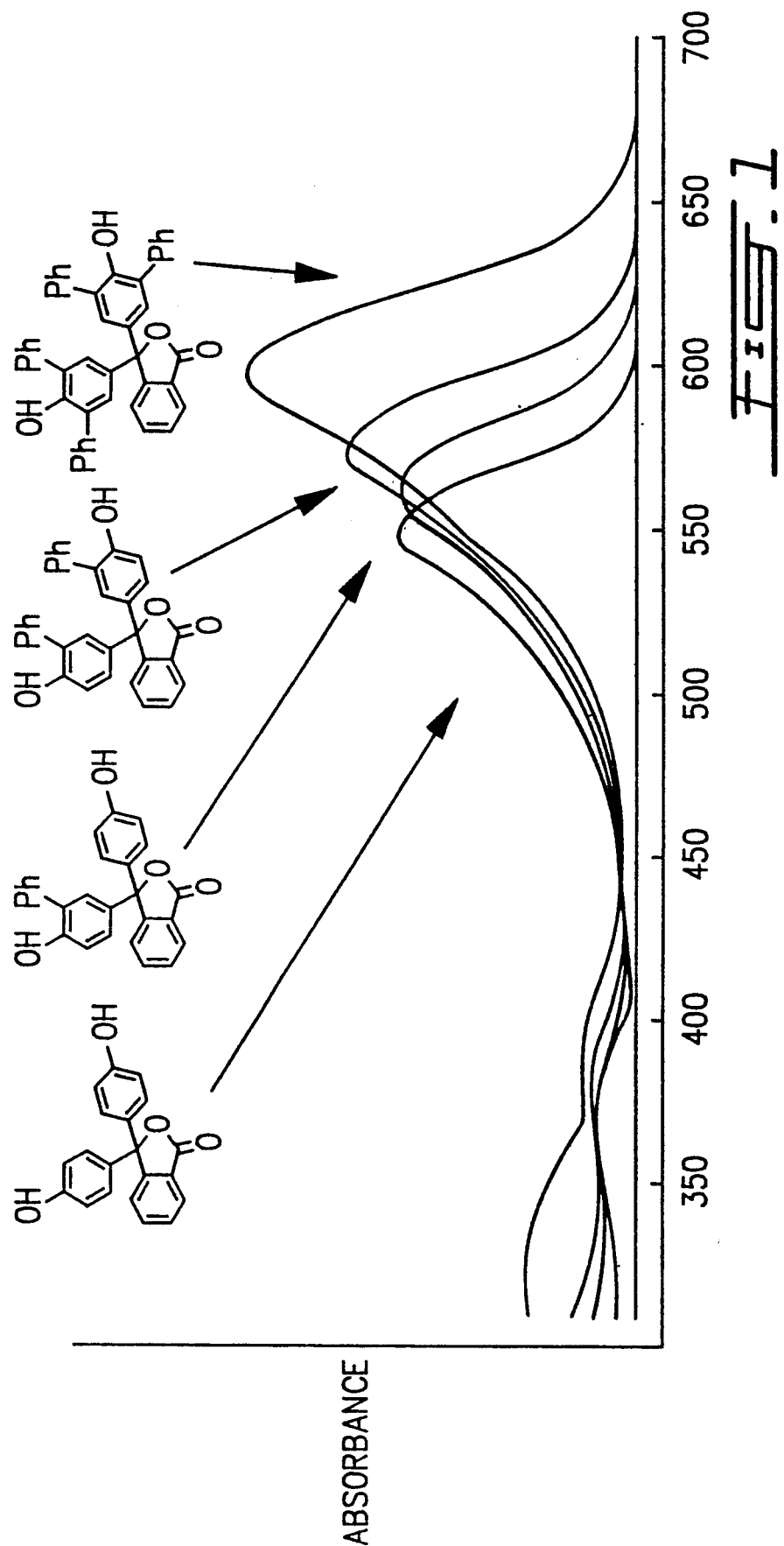
FIGURE 1 shows the UV visible spectra of phenyl-substituted phenolphthaleins of the invention.

With further reference to FIGURE 1, it can be seen that the phenolphthaleins (I) of the invention are indicator dyes and the colours in basic solution go from the deep red to phenolphthalein to blue colours with increase in the number of phenyl substituents.

EXPERIMENTAL

Materials. O-phenylphenol (Aldrich), 2,6-diphenylphenol (was kindly provided by the General Electric Company, methanesulfonic acid (Eastman Kodak), hydroxylamine hydrochloride (Aldrich), anhydrous potassium carbonate (Baker), potassium hydroxide (ACP Chemicals Inc.), sulfuric acid (A & C), hydrazine monohydrate (Aldrich), toluene (A & C), sulfolane (Aldrich), 4,4'-difluorophenylsulfone (Aldrich), 4,4'-difluorobenzophenone Aldrich), N-methylpyrrolidinone (NMP; Aldrich) reagent grade, dimethylacetamide (DMAc; Aldrich) reagent grade were used without purification.

Instrumentation. Molecular weight of the polymers were obtained relative to polystyrene standards in chloroform using a Waters 510 HPLC equipped with μStyragel columns (500, 103, 104 and 100 Å) arranged in series and a UV detector. 1H NMR were recorded at 200 or 270 MHz using a Varian XL-200 or a JOEL 270 CPF spectrometer, in CDCl3, CD30D, DMSO-d6 or acetone-d6. 13C NMR were recorded at 50 MHz or 67.5 MHz using a Varian XL-200 and JOEL 270 CPF spectrometer, respectively. IR were recorded using IR Analect AQS-18 FTIR spectrophotometer. Melting point of the intermediates and the monomers were obtained using Fisher-Johns melting point apparatus. Glass transition temperatures (Tg) of the polymers were obtained using a Seiko 220 DSC instrument at a heating rate of 10° C./min. in N2 (50 mL/min.). The weight loss data were obtained from a Seiko TG/DTA instrument at a heating rate of 10° C./min. in N2 and air (200 mL/min.). UV was measured using Unicam 850 spectrophotometer. Microanalyses were obtained from Guelph Chemical Laboratories Ltd., Guelph, Ontario, Canada. Mass spectroscopy was measured by Kratos MS25RFA analytical.

EXAMPLES

General procedure for the preparation of phenolphthalein derivatives 2a-d.

EXAMPLE 1

To a rb. flask equipped with a short column, phenolphthalein and a substituted phenol was added in a ratio of 1:5 respectively. Methanesulfonic acid (0.05 eq.) was added, and the reaction mixture was stirred in an oil bath at 135° C. for 48 hr. Following the reaction by thin layer chromatography (in CHCl3:acetone 98:2 respectively) two major spots were observed which refer to the mono and disubstituted derivatives of phenolphthalein. The excess of the substituted phenol was distilled off at 150° C. using a Kugelrohr distillation apparatus. The products, (2a and 2b), were isolated by flash chromatography (98:2 CHCl3:acetone). 2a is a crystalline products which was recrystallized from acetic acid. The monosubstituted derivatives 2b was obtained as an oil which didn't recrystallize. 2a,b were obtained in a total yield of 67%. The ratio 2a:2b (1.5:1).

3,3-bis[(4'-hydroxy-3'-phenyl)phenyl]isobenzofuranone 2a: mp 203° C.; 1H NMR (200MHz, CD3OD) d 7.82 (d, j=8.0 Hz, 1 H, CH-6), 7.63–7.08 (m, 17 H, ArH), 6.87 (d, j=8.5 Hz, 2 H, CH-5,5'), 4.87 (s, 2H, OH). 13C NMR (200 MHz, CD30D) d 172.5 (C=O), 94.02 (C-3), 139.98, 136.11, 133.80, 131.06, 130.06, 130.89, 130.62, 130.31, 129.40, 128.93, 128.30, 126.93, 126.61 125.80. UV-Vis (c=2×10-5M) lmax 572 (43000M) nm. MS (EI) m/e 470 (M+); Anal. Calcd for C32H2204: C, 81.7; H, 4.68; Found: C, 81.75; H, 4.95

.3-[(4'-hydroxy-3'-phenyl)phenyl]-3-(4''-hydroxyphenyl)isobenzofuranone 2b: 1H NMR (200 MHz, Acetone-d6) d 8.57 (dd, j=8.0 Hz, 1 H, CH-7), 7.90–6.79 (m, 15 H, ArH). UV-Vis (c=2×10-5M) lmax 560 (35000 M) nm.

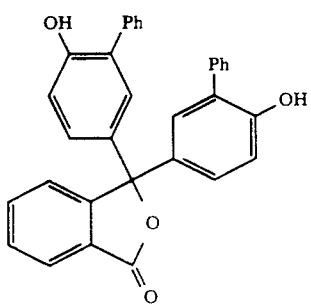

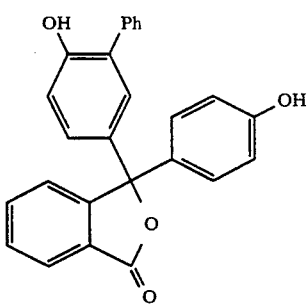

EXAMPLE 2

The reaction was carried out as in Example 1 using phenolphthalein and 2,6-diphenylphenol to produce the substituted phenolphthaleins 2c and 2c. 2c,d were obtained in a total yield of 52%. The ratio 2c:2d (3.7:1).

3,3-bis[(3'-5'-diphenyl-4'-hydroxy)phenyl]isobenzofuranone 2c: mp 274° C.; 1H NMR (200 MHz, CDC13) d 7.96 (s, 1 H, CH-7), 7.92 (s, 1 H, CH-4), 7.75–7.35 (m, 22 H, ArH), 7.30 (s, 4 H, CH-2',6',2",6"), 5.5. (s. 2 H, OH). UV-Vis (c=2×10-5 M) lmax 596 (57500M) nm. MS (EI) m/e 622 (M+); Anal. Calcd for C44H30O4: C, 84.87; H, 4.86; Found: C, 84.85; H; 4.86.

3-[(3',5'-diphenyl-4'-hydroxy)phenyl]-3-(4"-hydroxyphenyl)isobenzofuranone 2d: 1H NMR (200 MHz, CDC13) d 7.94 (d j=8.0 Hz, 1 H, CH-7), 7.78–7.35 (m, 13 H, ArH), 7.28 (s, 2 H, CH-2',6'), 7.25 and 6.82 (AB q, j=8.0 Hz, 4 H, CH-2",3",5",6"), 6.2 (s, 1 H, C-OH-4") 5.51 (s, 1 H, C—OH—4').

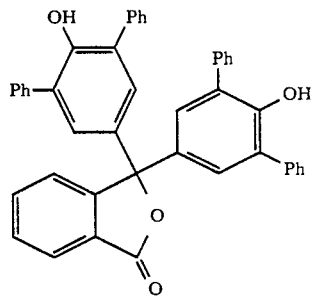

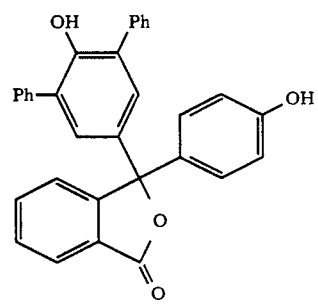

EXAMPLE 3

Preparation of 2-(4'-hydroxy-3'-phenylbenzoyl)benzoic acid 3a:

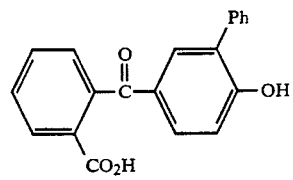

In a 100 mL. r.b. flask equipped with a short column there was added the disubstituted derivative of phenolphthalein (2a) (2.0 g, 0.00425 mol), hydroxylamine hydrochloride (0.34 g, 0.0049 mol), potassium hydroxide (1.428 g, 0.0255 mol) and 50 mL of H2O, and the mixture was stirred at 100° C. in an oil bath. The blue reaction mixture became homogeneous when it reached boiling. Within half an hour the colour had changed to brown. Following the reaction by thin layer chromatography (TLC) (20% EtOAc in hexane+3 drops AcOH), a new product was observed, but not all the starting material reacted. After 4 hr. no change had been observed and another portion of hydroxylamine hydrochloride (1.15 eq.) and potassium hydroxide (6.0 eq.) was added. An hour later, tlc indicated that no starting material remained. The reaction mixture was cooled to room temperature and it was acidified dropwise with concentrated H2SO4. A yellow precipitate was obtained. The reaction was stirred at 100° C. over night to complete the hydrolysis. The reaction mixture turned brown. It was filtered, washed 3x with hot diluted H2SO4 and then with H2O. It was recrystallized 2 x (EtOAc/charcoal) to give 0.8 g, (58.4% yield) of a white product; 3a: mp 273° C.; 1H NMR (200 MHz, DMSO-d6) d 10.63 (s, 1 H, COOH), 7.96 (d, j=8.0 Hz, 1 H, CH-6), 7.74–7.34 (m, 10 H, ArH), 7.02 (d, j=8.0 Hz, 1 H, CH-5'). MS (EI) m/e 318 (M+); Anal. Calcd for C20H14O4: C, 75.47; H, 4.40; Found: C, 75.46; H, 4.62.

EXAMPLE 4

Preparation of 2-(3',5'-diphenyl-4'-hydroxybenzoyl)-benzoic acid 3b:

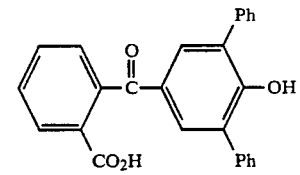

In a 250 mL r.b. flask equipped with a short column the disubstituted derivative of phenolphthalein (2c) (2.5 g, 0.0004 mol), hydroxylamine hydrochloride (0.64 g, 0.0092 mol), potassium hydroxide (2.856 g, 0.0510 mol) and 100 mL H2O were added and the mixture was refluxed at 100° C. in an oil bath with stirring for 48 hr. The blue reaction mixture turned green, but did not become homogeneous. Following the reaction by thin layer chromatography (TLC) (20% EtOAc in hexane+3 drops AcOH), a new product was observed, but not all the starting material reacted. The reaction was stopped and it was filtered to remove all the unreacted starting material. The filtrate contained the product and minor impurities. It was acidified dropwise with concentrated H2SO4. A yellow precipitate was obtained. It was stirred at 100° C. over night to complete the hydrolysis. The reaction mixture turned brown. It was filtered, washed 3 x with hot diluted H2SO4 and then with H2O. It was recrystallized 2 x EtOAc/charcoal) to give 0.63 g, (42% yield) of a white product; 3b: mp 234° C.; 1H NMR (200 MHz, CDC13) d 8.15 (dd, j=8.0 Hz, 1 H, CH-6), 7.70 (s, 2 H, CH-2',6'), 7.80–7.41 (m, 15 H, ArH). 13C NMR (200 MHz, CDC13) d 169.65 (COOH), 157.28 (c-4'), 143.62 (C-2), 139.43 (C-3',5'), 131.80, 131.51, 131.31, 131.07, 130.83, 129.86, 129.03, 128.96. IR (CDC13) 1710 cm-1 (COOH), 1666 cm-1 (C=O), 1584 cm-1 (Ar vib.); MS (EI) m/e 394 (M+); Anal. Found for C26H18O4: C, 79.19; H, 4.57; Found: C, 79.40; H, 4.66

General procedure for the preparation of the 1(2H)-Phthalazone derivatives 4 a–c:

EXAMPLE 5

Synthesis of 4c. To 1.0 eq. of 4'-hydroxybenzoyl-2-benzoic acid 3c, 1.5 eq. of hydrazine monohydrate was added. It was placed in a r.b. flask equipped with a short column, and dissolved in sulfolane at 100° C. in an oil bath with stirring to give a clear colorless solution. The phthalazine product precipitated out of the reaction mixture to give a white crystalline material. 4c precipitated out after ½ hr. It was cooled down to room temp. with stirring for 1.0 additional hour, filtered, and recrystallized from boiling ethanol to give white shiny crystals; 4(4-hydroxyphenyl)-1(2H)-phthalazone 4c: The product was obtained in 87% yield. mp 310° C.; 1H NMR (200, MHz, CD3OD) d 8.99–8.89 (m, 1 H, CH-5), 8.39–8.35 (m, 3 H, CH-6,7,8), 7.93 and 7.45 (AB q, j=8.0 Hz, 4 H, CH-2',3',5'6'). MS (EI) m/e 238 (M+); Anal. Calc for C14H10O2N2: C, 70.58; H, 4.23; N, 11.76 Found: C, 70.81; H, 4.14; N, 11.94.

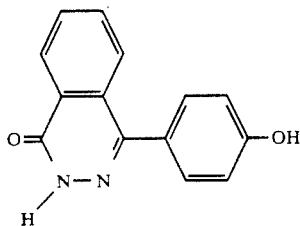

EXAMPLE 6

4(3-phenyl-4-hydroxyphenyl)-1-(2H)-phthalazone 4a: The product was obtained as in example 5 starting with 3a and hydrazine in 87.5% yield; mp 301° C.; 1H NMR (200 MHz, DMSO-d6) d 8.33 (dd=8.0 Hz, 1 H, CH-5), 7.97–7.79 (m, 4 H, ArH), 7.62 (d, j=8.0 Hz, 2 H, ArH) 7.54–7.22 (m, 6 H, ArH), 7.11 (d=8.0 Hz, 1 ArH). MS (EI) m/e 314 (M+) Anal. Calcd for C20H14O2N2: C, 76.43; H, 4.46; N, 8.92 Found: C, 76.43; H, 4.63; N, 9.13.

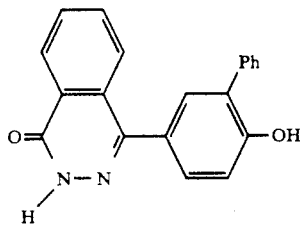

EXAMPLE 7

4(3,5-diphenyl-4-hydroxyphenyl)-1(2H)-phthalazone 4b: The product was obtained as in example 5 starting with 3a and hydrazine in 82.8% yield; mp 284° C.; 1H NMR (200, MHz, DMSO-d6) d 8.72 (d, j=4.0 Hz, 1 H, ArH), 8.33 (dd, j=8.0 Hz, 1 H, CH-5), 8.04–7.70 (m, 3 H, ArH), 7.62 (d, j=8.0 Hz, 4 H, ArH), 7.54–7.26 (m, 9 H, ArH). MS (EI) m/e 390 (M+); Anal. Calcd for C26H18O2N2: C, 79.98; H, 4.65; N, 7.17 Found: C, 79.64; H, 4.72; N, 7.28.

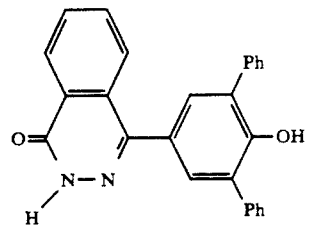

EXAMPLE 8

One pot reaction in preparation of the phthalazone derivatives 4a and 4b. The disubstituted derivatives of phenolphthalein 2a,2c were reacted with hydroxylamine hydrochloride in basic solution containing potassium hydroxide in water at 100° C. in an oil bath as in example 3 until the acids 3a,3b were obtained (as indicated by tlc). The reaction mixtures were acidified dropwise with concentrated H2SO4 to complete the hydrolysis and the reaction mixtures were refluxed over night. The brown precipitate was separated and was washed with hot dilute H2SO4 and hot H2O and used directly for the next step. It was dissolved in sulfolane at 100° C. and hydrazine was added. From the brown solution, the phthalazone products 4a,4b precipitated out. The mixture was stirred for another hour at room temperature, filtered and recrystallized from boiling ethanol/charcoal to give white crystals. 4a was obtained in total yield of 78% and 4b in total yield of 63.7% (2 steps).

EXAMPLES 9–14

General procedure for the preparation of poly(phthalazone ether sulfone)s and poly(phthalazone ether ketone)s. To a dry 100 mL 3-neck flask equipped with a Dean-Stark trap, a cold water condenser, magnetic stirrer, thermometer and nitrogen inlet, the phthalazone monomer was added together with 1.0 eq. of 4,4'-difluorodiphenylsulfone or 4,4'-difluorobenzophenone, 1.4 eq. of anhydrous potassium carbonate, N,N-dimethylacetamide (DMAC) to form a 20% solution and toluene was added. The mixture was heated to reflux. The temperature was maintained between 130°–140° C. for 5 hr. to ensure complete dehydration, then it was increased to 165°–170° C. and slow reflux was continued. The solution went from clear yellow to viscous brown. Aliquots were taken occasionally and precipitated into methanol solution to follow the polymerization reaction. The reaction mixture was diluted with DMAc, and was added dropwise to a beaker containing methanol: H2O (3:2) with vigorous stirring. The polymer was filtered and dried with suction. It was redissolved in CHCl3, filtered through a bed of celite and reprecipitated in methanol. After filtering, it was dried with suction and then in a vacuum oven at 80° C. over night. The yields range between 80–95%. All polymers were characterized and the results are summarized in Table I. Polymer 6b came out of solution within 6 hr. of polymerization time. It was dissolved and purified in NMP and precipitated in methanol: H2O (3:2) solution. Inherent viscosity was measured in NMP at 25.5° C. Polymer 6b gave only oligomers when DMAc, NMP, DMSO, n-methylcaprolactam, diphenylsulfone were used as a solvent. High molecular weight polymer was obtained within 2 hr. as judged by the large increase in solution viscosity using sulfolane as a solvent at 235° C. (35% solution) and the polymer then came out of solution. It was dissolved in phenol and precipitated hot in methanol: H2O (3:2) solution with vigorous stirring. A white polymer was obtained. It was purified by dissolving in a small amount of TFA and diluted with CHCl3 and reprecipitated in methanol and ammonium hydroxide. The white fibrous polymer was filtered with suction and dried in the vacuum oven over night. Inherent viscosity was measured in TFA: CHCl3 (2:18) mL at 25° C. Properties of Polymers of the Examples are shown in Table 1 below:

2. A process of producing a phthalazone of formula (VII):

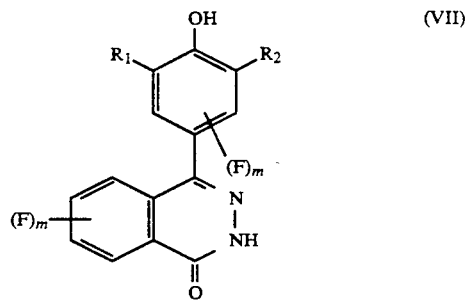

wherein $R_1$ and $R_2$ are both phenyl and each m, which may be the same or different is an integer of 0, 1, 2 or 4,

TABLE 1

| Example | Polymer | Polymerization Time (hr.) | Tg °C.[a] | Yield % | TGA (air/N2)[b] | $\eta inh$[c] | Mw | Mn |
|---|---|---|---|---|---|---|---|---|
| 9 | 6a | 18 | 294.5 | 92 | 505/505 | 0.38 | 43570 | 19804 |
| 10 | 6b | 2 | 253 | 95 | 489/485 | 0.47[d] | | |
| 11 | 7a | 72 | 274 | 92 | 507/491 | 0.51 | 54863 | 28338 |
| 12 | 7b | 7 | 252.5 | 95 | 481/478 | 0.86[e] | | |
| 13 | 8a | 72 | 293.4 | 81 | 501/496 | 0.25 | 25534 | 11876 |
| 14 | 8b | 72 | 271.2 | 75 | 498/496 | 0.22 | 18858 | 9110 |

[a]DSC at 20° C./min.
[b]TG/DTA 5% weight loss at 10° C./min.
[c]Inherent viscosity at concentration (0.5 g/dL) of CHCl3 at 25° C.
[d]Inherent viscosity at concentration (0.5 g/dL) of TFA/CHCl3 at 25° C.
[e]Inherent viscosity in concentration (0.5 g/dL) of NMP at 25.5° C.
[f]Molecular weights were obtained by gel permeation chromatography relative to polystyrene standards in CHCl3 at 25° C.

I claim:
1. A phthalazone of formula (VII):

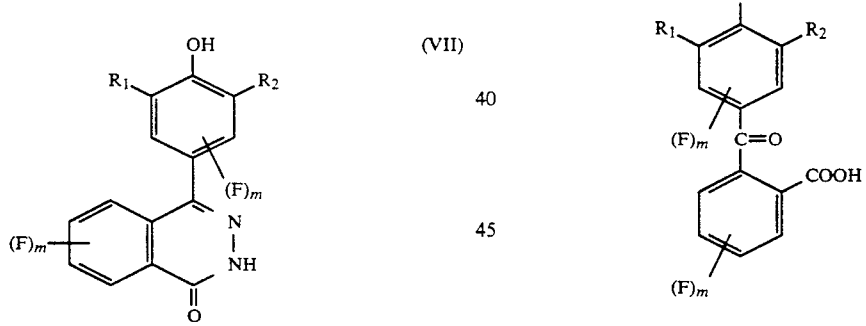

wherein $R_1$ and $R_2$ are both phenyl and each m, which may be the same or different is an integer of 0, 1, 2 or 4.

which comprises reacting a hydroxybenzoylbenzoic acid of formula (V):

wherein $R_1$, $R_2$ and m are as defined above, with hydrazine.

* * * * *